United States Patent
Ein-Gal

(10) Patent No.: US 8,178,855 B2
(45) Date of Patent: May 15, 2012

(54) VARIABLE SPATIAL BEAM MODULATOR

(76) Inventor: Moshe Ein-Gal, Ramat Hasharon (IL)

( * ) Notice: Subject to any disclaimer, the term of this patent is extended or adjusted under 35 U.S.C. 154(b) by 274 days.

(21) Appl. No.: 12/711,267

(22) Filed: Feb. 24, 2010

(65) Prior Publication Data
US 2011/0204260 A1   Aug. 25, 2011

(51) Int. Cl.
*G21K 5/10* (2006.01)
(52) U.S. Cl. ............ 250/492.22; 250/492.1; 250/492.2; 250/492.3; 378/158
(58) Field of Classification Search ............... 250/505.1, 250/506.1, 507.1, 515.1, 519.1, 492.1, 492.2, 250/492.22, 492.3, 492.23; 378/156, 158
See application file for complete search history.

(56) References Cited

U.S. PATENT DOCUMENTS
6,108,403 A * 8/2000 Cooper et al. ............... 378/156
* cited by examiner

*Primary Examiner* — Michael Maskell
*Assistant Examiner* — H. C.
(74) *Attorney, Agent, or Firm* — Dekel Patent Ltd.; David Klein

(57) ABSTRACT

For use with an irradiation system including a radiation source operable to produce a radiation beam towards a target, a beam modulator including a flexible, deformable container at least partially filled with a radiation attenuating fluid, a non-deformable first contacting surface in contact with a first portion of the container, the first contacting surface pivotable about a first axis, and a positioner operable to rotate the first contacting surface about the first axis, wherein as the first contacting surface rotates about the first axis, the first contacting surface deforms the container.

14 Claims, 1 Drawing Sheet

VARIABLE SPATIAL BEAM MODULATOR

FIELD OF THE INVENTION

The present invention relates generally to irradiation systems with radiation protection, and particularly to such a system with a variable wedge-like beam modulator.

BACKGROUND OF THE INVENTION

Many irradiation systems use attenuation to modulate a radiation beam in an effort to keep radiation at safe levels to tissues which are to be protected from harmful radiation. The radiation beam irradiating a target in an object is attenuated between the object surface and the target. The target dose distribution perpendicular to the beam may be non-uniform due to spatially non-uniform attenuation, e.g., when the object surface is not perpendicular to the beam.

FIG. 1 illustrates an attenuating wedge 1 used in the prior art. The attenuating wedge 1 is placed in front of an object 2 that has a target 3, which causes the total attenuation of a radiation beam 4 to be the sum of the wedge attenuation and that of the object. The wedge is thus used for compensating target non-uniform dose distribution.

Since object attenuation depends on beam/object orientation, a different wedge may be required for different orientations. Continuously varying orientations, such as during an arc treatment, may require rapid wedges exchange which is technically and economically prohibitive.

U.S. Pat. No. 6,836,535 to Toth et al. describes a filtering apparatus for a CT or x-ray imaging system. The filtering apparatus moves along an axis with respect to an attenuation pattern of a subject during an imaging session to reduce radiation exposure to sensitive anatomical regions of the subject. In one embodiment, the filtering apparatus includes a flexible bladder containing attenuating fluid positioned between an upper plate and a lower plate. The bladder is sufficiently flexible such that the attenuating fluid contained therein may be modulated or manipulated to define the desired attenuation profile. The bladder may contain attenuating liquid, gelatin, beads, or the like. The upper plate is fabricated from a flexible x-ray transparent material such as plastic that, in response to an applied force, alters the shape of the flexible bladder. The lower plate supports the flexible bladder and is fabricated from a solid x-ray transparent material. The flexible bladder and lower and upper plates are each fabricated from an x-ray transparent material so that x-rays are attenuated primarily by the attenuating fluid rather than the bladder or plates.

SUMMARY OF THE INVENTION

The present invention seeks to provide an irradiation system (e.g., for stereotactic radiotherapy) with a variable spatial beam modulator, as is described more in detail hereinbelow. The modulator may be operable to continuously vary beam modulation according to the beam/object orientation.

It is noted that the present invention provides a different structure and concept than the prior art. For example, U.S. Pat. No. 6,836,535 uses a bladder filled with attenuating material wherein a flexible plate is deformed to exert force on the bladder. The plates are not rotated. In contrast, in the present invention, rigid, non-deformable contacting surfaces (e.g., plates) are used with a flexible, deformable container (bladder). The non-deformable plates are rotated on sides of the bladder such that attenuation variations are achieved in one or more directions.

There is thus provided in accordance with an embodiment of the present invention, for use with an irradiation system including a radiation source operable to produce a radiation beam towards a target, a beam modulator including a flexible, deformable container at least partially filled with a radiation attenuating fluid, a non-deformable first contacting surface in contact with a first portion of the container, the first contacting surface pivotable about a first axis, and a positioner operable to rotate the first contacting surface about the first axis, wherein as the first contacting surface rotates about the first axis, the first contacting surface deforms the container. The first axis may be generally perpendicular to a propagation axis of the radiation beam.

In accordance with an embodiment of the present invention the beam modulator further includes a non-deformable second contacting surface in contact with a second portion of the container different from the first portion, the second contacting surface pivotable about a second axis, and a positioner operable to rotate the second contacting surface about the second axis, wherein as the second contacting surface rotates about the second axis, the second contacting surface deforms the container. The second axis may be generally perpendicular to a propagation axis of the radiation beam. The second axis may be same or different than the first axis (e.g., generally perpendicular to the first axis).

In accordance with an embodiment of the present invention the positioner that positions the first contacting surface is the positioner that positions the second contacting surface.

In accordance with another embodiment of the present invention the positioner that positions the first contacting surface is separate from the positioner that positions the second contacting surface.

In accordance with an embodiment of the present invention the positioner is in communication with an orientation changer, wherein the orientation changer is operable to change an orientation of the beam and the target.

In accordance with an embodiment of the present invention the positioner is operable to translate at least one of the first and second contacting surfaces.

The container is preferably made of an elastomeric material, and the first and second contacting surfaces are preferably generally radiation transparent.

There is also provided in accordance with an embodiment of the present invention, for use with an irradiation system including a radiation source operable to produce a radiation beam towards a target, a beam modulator including a flexible, deformable container at least partially filled with a radiation attenuating fluid, a plurality of non-deformable contacting surfaces in contact with a plurality of portions of the container, the contacting surfaces pivotable about a plurality of pivot axes, and a positioner system operable to rotate the contacting surfaces about the pivot axes, wherein as the contacting surfaces rotate about the pivot axes, the contacting surfaces deform the container.

There is also provided in accordance with an embodiment of the present invention an irradiation system including a radiation source operable to produce a radiation beam towards a target, and a beam modulator including a flexible, deformable container at least partially filled with a radiation attenuating fluid, a plurality of non-deformable contacting surfaces in contact with a plurality of portions of the container, the contacting surfaces pivotable about a plurality of pivot axes, and a positioner system operable to rotate the contacting surfaces about the pivot axes, wherein as the contacting surfaces rotate about the pivot axes, the contacting surfaces deform the container.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
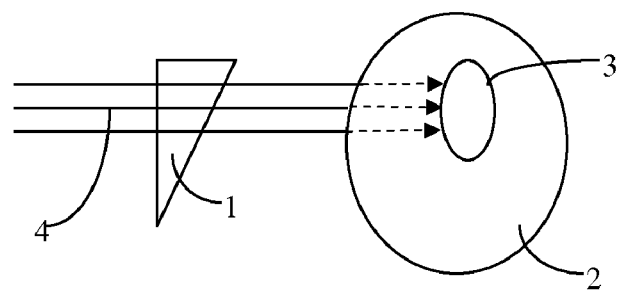
FIG. 1 is a simplified illustration of an attenuating wedge used in the prior art.
Figure 2:
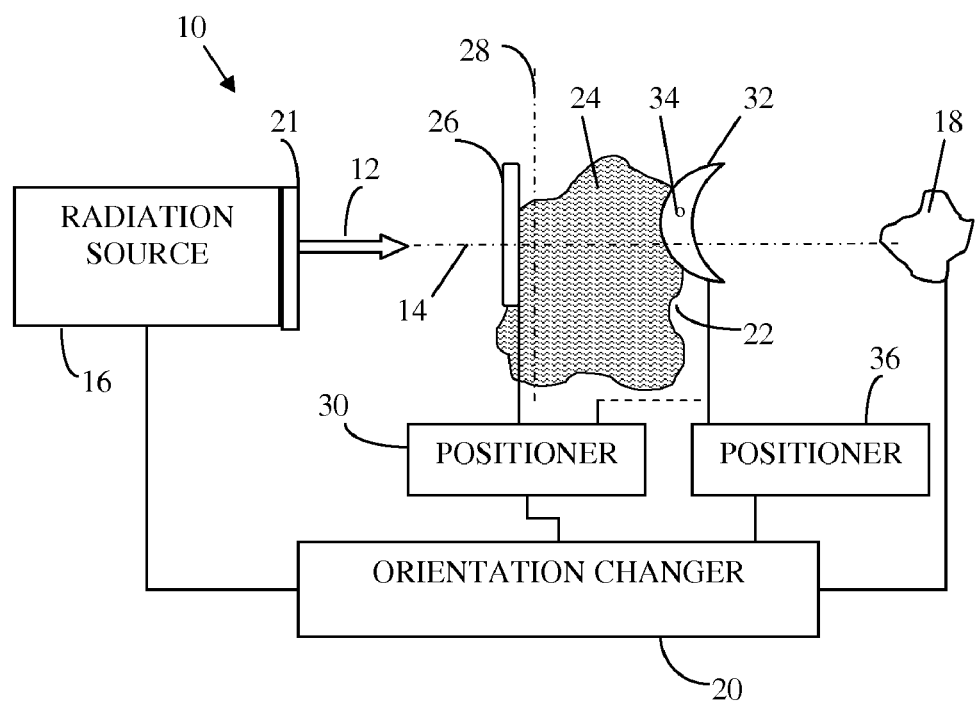
FIG. 2 is a simplified illustration of an irradiation system with a variable spatial beam modulator, constructed and operative in accordance with an embodiment of the present invention.

Reference is now made to FIG. 2, which illustrates an irradiation system 10 with a variable spatial beam modulator, constructed and operative in accordance with an embodiment of the present invention.

System 10 may be an isocentric radiotherapy system, wherein a radiation beam 12 is emitted along a beam axis 14 by a radiation source 16 is oriented toward a target 18 from a discrete or continuous set of orientations. (Radiation source 16 may be any suitable radiation source, stationary or movable, such as but not limited to, a cobalt source, LINAC, etc.) Isocentricity refers to rotation of the radiation source 16 and/or the target 18 about a target rotational axis typically intersecting the target. In such a system, an orientation changer 20 is provided operable to change an orientation of the beam 12 and the target 18. For example, the orientation changer 20 may be a rotating gantry that cooperates with a turntable, and which can operate with various sensors, fiduciary markers and processors to move the beam and target in accordance with a treatment plan.

System 10 may also include a beam shaper 21 (e.g., a multileaf collimator) operable to collimate the radiation beam 12 according to a shape of the target 18.

In accordance with a non-limiting embodiment of the present invention, the variable spatial beam modulator includes a flexible, deformable container 22 at least partially filled with a radiation attenuating fluid 24, such as but not limited to, water, mercury or liquid compounds of iodine, thallium, and any other liquid or suspension that exhibits radiation attenuating properties. The container 22 is preferably made of an elastomeric material, such as but not limited to, natural or synthetic rubber.

A non-deformable first contacting surface 26, such as but not limited to, a plate, disk bar and the like, contacts a first portion of container 22. The first contacting surface 26 pivots about a first pivot axis 28. A positioner 30, such as but not limited to, a servomotor, step motor and the like, rotates the first contacting surface 26 about first axis 28. As the first contacting surface 26 rotates about first axis 28, the first contacting surface 26 pushes against and deforms container 22. The first axis 28 may be generally perpendicular to propagation axis 14 of radiation beam 12.

In accordance with an embodiment of the present invention, the beam modulator includes many (two, three or more) contacting surfaces. For example, in the illustrated embodiment, a non-deformable second contacting surface 32 is in contact with a second portion of container 22 (different from the first portion). The second contacting surface 32 pivots about a second axis 34. A positioner (either the first positioner 30 or another positioner 36) rotates the second contacting surface 32 about the second axis 34. As the second contacting surface 32 rotates about the second axis 34, the second contacting surface 32 pushes against and deforms container 22. The second axis 34 may be generally perpendicular to propagation axis 14 of radiation beam 12. The second axis 34 may be the same or different than the first axis 28 (e.g., generally perpendicular to first axis 28).

The contacting surfaces are preferably made of a radiation transparent material, such as but not limited to, glass, plastic, or advanced engineering materials, such as crystalline magnesium fluoride or crystalline lithium fluoride. As shown in FIG. 2, the contacting surfaces can have different shapes, such as but not limited to, rectangular (prismatic, regular polyhedron), crescent shaped, round, oval, ellipsoid and many others.

In one embodiment, positioner 30/36 is in communication with orientation changer 20, so that the movement of contacting surfaces, and thus the attenuation of beam 12 by means of the change in shape of container 22, is coordinated with the change in orientation of beam 12 and target 18.

In accordance with an embodiment of the present invention, positioner 30/36 not only rotates but also translates one or all of the contacting surfaces, in which case the positioner includes a linear actuator or the like, for example.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. For use with an irradiation system comprising a radiation source operable to produce a radiation beam towards a target, a beam modulator comprising:
    a flexible, deformable container at least partially filled with a radiation attenuating fluid;
    a non-deformable first contacting surface in contact with a first portion of said container, said first contacting surface pivotable about a first axis; and
    a positioner operable to rotate said first contacting surface about said first axis, wherein as said first contacting surface rotates about said first axis, said first contacting surface deforms said container.

2. The beam modulator according to claim 1, wherein said first axis is generally perpendicular to a propagation axis of the radiation beam.

3. The beam modulator according to claim 1, further comprising a non-deformable second contacting surface in contact with a second portion of said container different from said first portion, said second contacting surface pivotable about a second axis, and a positioner operable to rotate said second contacting surface about said second axis, wherein as said second contacting surface rotates about said second axis, said second contacting surface deforms said container.

4. The beam modulator according to claim 3, wherein said second axis is generally perpendicular to a propagation axis of the radiation beam.

5. The beam modulator according to claim 3, wherein said second axis is different than said first axis.

6. The beam modulator according to claim 3, wherein said second axis is generally perpendicular to said first axis.

7. The beam modulator according to claim 3, wherein said positioner that positions said first contacting surface is the positioner that positions said second contacting surface.

8. The beam modulator according to claim 3, wherein said positioner that positions said first contacting surface is separate from the positioner that positions said second contacting surface.

9. The beam modulator according to claim 3, wherein said positioner is operable to translate at least one of said first and second contacting surfaces.

10. The beam modulator according to claim 3, wherein said first and second contacting surfaces are generally radiation transparent.

11. The beam modulator according to claim 1, wherein said positioner is in communication with an orientation changer, wherein said orientation changer is operable to change an orientation of the beam and the target.

12. The beam modulator according to claim 1, wherein said container is made of an elastomeric material.

13. For use with an irradiation system comprising a radiation source operable to produce a radiation beam towards a target, a beam modulator comprising:

a flexible, deformable container at least partially filled with a radiation attenuating fluid;

a plurality of non-deformable contacting surfaces in contact with a plurality of portions of said container, said contacting surfaces pivotable about a plurality of pivot axes; and a positioner system operable to rotate said contacting surfaces about said pivot axes, wherein as said contacting surfaces rotate about said pivot axes, said contacting surfaces deform said container.

14. An irradiation system comprising:

a radiation source operable to produce a radiation beam towards a target; and a beam modulator comprising:

a flexible, deformable container at least partially filled with a radiation attenuating fluid;

a plurality of non-deformable contacting surfaces in contact with a plurality of portions of said container, said contacting surfaces pivotable about a plurality of pivot axes; and a positioner system operable to rotate said contacting surfaces about said pivot axes, wherein as said contacting surfaces rotate about said pivot axes, said contacting surfaces deform said container.

* * * * *